United States Patent [19]
Barber

[11] Patent Number: 5,489,301
[45] Date of Patent: Feb. 6, 1996

[54] CORNEAL PROSTHESIS

[76] Inventor: John C. Barber, 590 Squaw Run Road E., Pittsburgh, Pa. 15238

[21] Appl. No.: 116,895

[22] Filed: Sep. 3, 1993

[51] Int. Cl.$^6$ ..................................................... A61F 2/14
[52] U.S. Cl. ............................................................ 623/5
[58] Field of Search .............................................. 623/4, 5

[56] References Cited

U.S. PATENT DOCUMENTS

| | | | |
|---|---|---|---|
| 3,458,870 | 8/1969 | Stone | 3/13 |
| 3,971,670 | 7/1976 | Homsy | 156/196 |
| 3,992,221 | 11/1976 | Homsy et al. | 134/16 |
| 3,992,725 | 11/1976 | Homsy | 3/1 |
| 4,118,532 | 10/1978 | Homsy | 428/294 |
| 4,127,902 | 12/1978 | Homsy | 3/1 |
| 4,129,470 | 12/1978 | Homsy | 156/155 |
| 4,209,480 | 6/1980 | Homsy | 264/108 |
| 4,455,690 | 6/1984 | Homsy | 3/1 |
| 4,576,608 | 3/1986 | Homsy | 623/11 |
| 4,923,466 | 5/1990 | Pentucci | 623/5 |
| 5,300,115 | 4/1994 | Py | 623/4 |

OTHER PUBLICATIONS

Barber J. C. Keratoprostheses: Past And Present. International Ophthalmology Clinics 1988; 28(2):103–109.
J. Worst Research Group. Keratoprostheses: Surgical Stages of Keratoprosthesis Insertion. Nov. 6, 1992.

*Primary Examiner*—Randy C. Shay
*Attorney, Agent, or Firm*—Reed Smith Shaw & McClay

[57] ABSTRACT

An improved corneal prosthesis is comprised of an optical core member having a frustoconical shape and preferably a substantially cylindrical anterior section and a substantially conical posterior section. The optical core member of an alloplastic material, preferably intraocular grade polymethylmethacrylate, has an anterior flange portion extending peripherally about the anterior optical end portion of the core member at least about 0.5 and preferably less than 1.0 millimeter. A skirt member extends peripherally about and is attached, preferably mechanically, to the optical core member at a peripheral groove between the anterior section and the posterior section and is capable of being implanted in a lamellar pocket in the eye. The skirt member is of a hydrophylic porous semi-flexible material, preferably porous polytetrafluoroethylene, porous polytetrafluoroethylene carbon or porous polytetrafluoroethylene aluminum oxide fibers, has anterior and posterior contact surfaces with a total area greater than about 100 square millimeters, and preferably has a flexure modulus of a porous polytetrafluoroethylene aluminum oxide fiber sheet of between 0.15 and 0.30 millimeter in thickness. Preferably the diameter of the skirt member is at least about 9.5 millimeters and more preferably extends to within 1 to 2 millimeters of the limbus when the prosthesis is implanted in an eye.

20 Claims, 1 Drawing Sheet

CORNEAL PROSTHESIS

FIELD OF THE INVENTION

This invention relates to corneal prostheses used to replace all or part of the cornea of an eye.

BACKGROUND OF THE INVENTION

Many researchers have designed corneal prostheses and hundreds have been implanted. Pellier de Quengsy is credited with first suggesting the insertion of a glass plate into the cornea in 1771. These various designs met with varying degrees of early success, some with initial enthusiasm, and generally by disillusionment as the long-term complications occurred. Barber J. C., *International Ophthalmology Clinics*, 28:103–09 (1988).

Early corneal prosthesis designs involved imbedding a flat disk of alloplastic material into the cornea with a hole anterior to the prosthesis. Spool-shaped optical lenses were then placed in the hole through the cornea and the prosthesis. Another early design was an optical core held by plates attached to the core and engaging the anterior and posterior surfaces of the cornea. The posterior plate was inserted through an opening formed in the cornea, with a trephine and a relaxing incision which was the source of considerable complications.

Later, a two-piece, collar-button prosthesis was designed in which either an anterior or posterior plate was placed on a mushroom shaped part of the prosthesis, after the posterior plate was inserted through the cornea. This design was technically difficult and required special tools. Dohlman assembled his prosthesis of this design in a donor cornea before operating. Dohlman C. H., *American Journal of Ophthalmology*, 77:694–700 (1974). Dohlman used methylchloride to bond the two prosthetic pieces together, and, in some cases, also glued the prosthesis to the cornea with cyanoacrylate. The donor assembly was then sewn into the cornea of the patient during surgery as a penetrating keratoplasty.

More recent corneal prosthesis designs have had an optical core member held by a skirt or flange. Cardona H., *American Journal of Ophthalmology*, 54:284–94 (1962); Choyce D. P., *Ophthalmic Surgery*, 8:117–26 (1977). Cordona initially attached the skirt to the optical core member, but later went to a two-piece, nut-and-bolt design to allow adjustment of the height of the core above the conjunctiva. Choyce also used the two-piece design for adjustment in an early optical core-skirt prosthesis, as well as to facilitate removal of retroprosthetic membranes over the posterior surface of the core. Choyce buried the skirt with a flush core until the skirt was integrated into the cornea, and then replaced the original core with the optical core in a separate procedure.

The radial relaxing incision used in implanting these early prostheses was believed to be one of the reasons for their failure. As a result, Cardona developed a design in which the skirt of the prosthesis was placed in a lamellar pocket with the optical core extending anteriorly and posteriorly through the skirt. To avoid the relaxing incision, the lamellar pocket was made by a perilimbal incision before the central cornea was opened with a trephine. Melting occurred around the optical core with this design causing leakage, infection and extrusion. The intralamellar skirt was fenestrated to allow diffusion of nutrients and to increase incorporation into the tissue. Stone W. Jr., *American Journal of Ophthalmology*, 39(2):185–96 (1955); Choyce D. P., *Ophthalmic Surgery*, 8:117–26 (1977).

With the optical core and skirt designs of corneal prostheses, many skirt materials have been studied, including glass, polymethylmethacrylate, silicone, Teflon, Dacron, siliconed Teflon, Silastic, fiberglass, nylon, cellulose and a ceramic of aluminum oxide. Cardona H., *American Journal of Ophthalmology*, 64:228–33 (1967); Polack F. M. et al, *Ophthalmology*, 87:693–98 (1980); Polack F. M., *British Journal of Ophthalmology*, 55:838–43 (1971); Polack F. M., *Cornea*, 2:185–96 (1983); Kozarsky A. M. et al, *Ophthalmology*, 94:904–11 (1987); Heimke G. et al, *Cornea*, 2:197–201 (1983). Silicone was too soft and was found to become cloudy after some time period, fiberglass caused heavy vascularization and extrusion, and nylon worked well for awhile but later extruded. Cellulose caused inflammation, ulceration, opacification and extrusion. The ceramic of aluminum oxide showed early promise but mechanical problems and later complications prevailed. Of these materials, Dacron and siliconed Teflon proved to be the best, out these presented complications because of enzymatic degradation. These designs typically utilized a clinical grade (intraocular grade) polymethylmethacrylate or silicone optical core member of 2 to 5 millimeters in diameter, with the skirt of one of the above named materials having an outer diameter typically of 5 to 8 millimeters and glued or mechanically attached to the optical core member.

In an effort to obtain better biocompatibility, Strampelli and Marchi used tooth and bone to form the skirt to hold the optical core member in place. Strampelli B. et al, *Ann Ottalmol Clin Ocul*, 96:1–57 (1970). Blencke and colleagues tried to improve on this design by replacing the tooth with a glass ceramic. Blencke B. A. et al, *Ophthalmologica*, 176:105–12 (1978). However, incorporation of the prosthesis material into the corneal tissue proved to be a necessity. Glass, polymethylmethacrylate, cellulose and other nonporous materials did not allow for invasion by the fibrous tissue or vessels. Fibrovascular invasion of implant material has been demonstrated with porous polytetrafluoroethylene carbon fibers (Proplast), porous meltblown polybutylene, large pore Dacron mesh, expanded polytetrafluoroethylene (Gore-Tex) and porous polyethylene (Plastipore). Barber J. C. et al, *Investative Ophthalmology and Visual Science*, 19:182–90 (1980); Girard L. J., *Cornea*, 2:207–24 (1983); Trinkaus-Randall V. et al, Fifteenth Cornea Research Conference, Boston, September 1987; Kaiser D., *Thorac Cardiovascular Surgery*, 33:239–43 (1985); Dreikorn K. et al, *Urology Research*, 7:19–21 (1979). Of these skirt materials, expanded polytetrafluoroethylene, porous polyethylene and porous polytetrafluoroethylene carbon fibers have provided for good tissue growth, but long term complications have caused the prosthesis designs with these skirt materials to be unsuccessful due to melting, leakage and extrusion. Also, the prosthesis was often first installed in a remote site in the patient, such as a cheek, to allow growth of tissue around the skirt so that when later transplanted into the cornea the prosthesis had an increased likelihood of long-term stability.

Another problem with corneal prostheses of these various designs was overgrowth of the conjunctiva across the anterior surface of the optical core member, or the retraction and melting of the conjunctival tissue around the optical core member. Cardona H., *American Journal of Ophthalmology*, 54:284–94 (1962); Choyce D. P., *Ophthalmic Surgery*, 8:117–26 (1977). Cordona and Choyce reported that this is a function of the height of the optical core above the anterior conjunctival surface, and used an adjustable optical core to vary the anterior protrusion of the core preventing overgrowth. However, the anterior protrusion created problems as movement of the upper eyelid caused mechanical movement of the prosthesis and disrupted the stability of the means holding the prosthesis in place. This mechanical movement in turn caused enzymatic degradation, leakage and extrusion.

SUMMARY OF THE INVENTION

The corneal prosthesis of the present invention is comprised of an optical core member of alloplastic material, preferably intraocular grade polymethylmethacrylate, having a substantially frustoconical shape, and a skirt member extending peripherally about and being attached to the core member preferably mechanically by a groove in the core member. The optical core member has an anterior first optical end portion and a posterior second optical end portion capable of optically transmitting light from the exterior of an eye to a retina of an eye when the prosthesis is implanted in the cornea. At the first optical end portion, the optical core member has an anterior flange portion extending peripherally at least about 0.5 and preferably less than 1.0 millimeter beyond the corse member. The anterior flange portion is capable of inhibiting the conjunctiva from growing over the optical surface of the first optical end portion when the prosthesis is implanted in an eye and is not so extensive as to cause enzymatic degradation to the conjunctiva adjacent the anterior flange portion.

Preferably the core member has an anterior section adjacent the first optical end portion, and a posterior section adjacent the second optical end portion. The anterior section may be slightly conical toward or away from where the skirt member is attached to the optical core member, but is preferably substantially cylindrical so as to be axial force neutral in urging lamellar tissue toward or away from the skirt member as explained in more detail in the preferred embodiments. The anterior section of the core member is preferably between about 0.8 and 1.2 millimeters in length from the anterior flange. The length of the anterior section is such as to allow the first optical end portion of the optical core member to extend anterior of the conjunctiva surface surrounding the implanted prosthesis and not cause instability to the prosthesis by movement of the eyelid. The preferred peripheral groove is capable of providing the mechanical attachment of the skirt member to the optical core member without the use of adhesive material.

The posterior section of the optical core member is substantially conical and preferably with a flare of 20 to 30 degrees toward the second optical end portion. When the prosthesis is implanted in an eye, the posterior conical section engages and urges the lamellar tissue toward the skirt member as explained in more detail in the preferred embodiments.

The skirt member is positioned spaced from the first optical end portion of the optical core member and is capable of being implanted in a lamellar pocket in an eye with the assembled prosthesis. The skirt member is of a hydrophilic porous semi-flexible material capable of vascularization and formation of fibrous tissue therein when implanted in an eye, and has anterior and posterior contact surfaces with the total area greater than about 100 square millimeters. The skirt member is preferably of a material selected from the group consisting of porous polytetrafluoroethylene, porous polytetrafluoroethylene carbon fibers and porous polytetrafluoroethylene aluminum oxide fibers, with porous polytetrafluoroethylene aluminum oxide fibers being most preferred. The skirt member preferably has a flexure modulus of porous polytetrafluoroethylene aluminum oxide fiber sheet between about 0.15 and 0.30 millimeter in thickness to provide distribution of the reactive forces to the forces exerting axially on the optical core member to extrude the prosthesis when it is implanted. The skirt member also preferably has a diameter greater than 9.5 millimeters and preferably 10 to 11 millimeters. More preferable, the diameter of the skirt member extends to within 2 and preferably 1 millimeter of the limbus when the prosthesis is implanted in an eye. Also preferably the skirt member has a bevel peripherally about the anterior contact surface so as to avoid pressure necrosis on implantation. The skirt member provides for rapid and long-term stable positioning of the prosthesis in an eye on implantation, and eliminates, for example, the procedure of implanting the prosthesis in a donor cornea or other site within a patient to provide tissue growth and enable the prosthesis to be properly stabilized for long-term use when implanted in an eye.

Other details, objects and advantages of the present invention will become more readily apparent from the following description of the presently preferred embodiments thereof.

BRIEF DESCRIPTION OF THE DRAWINGS

In the accompanying drawings, preferred embodiments of the present invention are illustrated, wherein.

DESCRIPTION OF THE PREFERRED EMBODIMENTS

Figure 1:
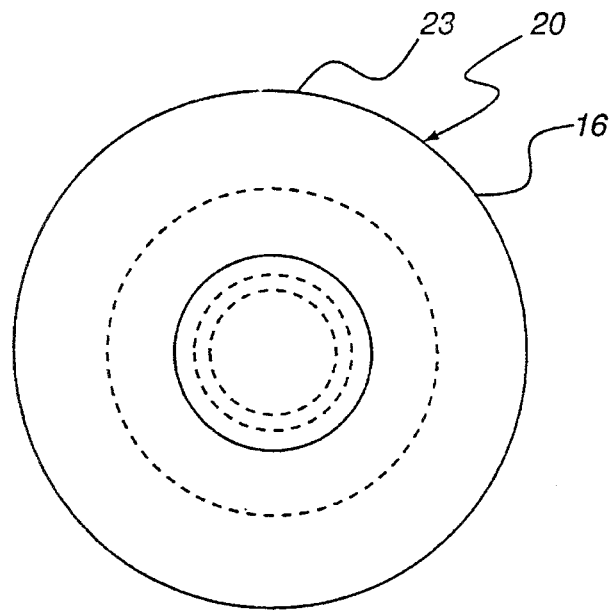
FIG. 1 is an elevational view of a preferred embodiment of the present invention.
Figure 2:
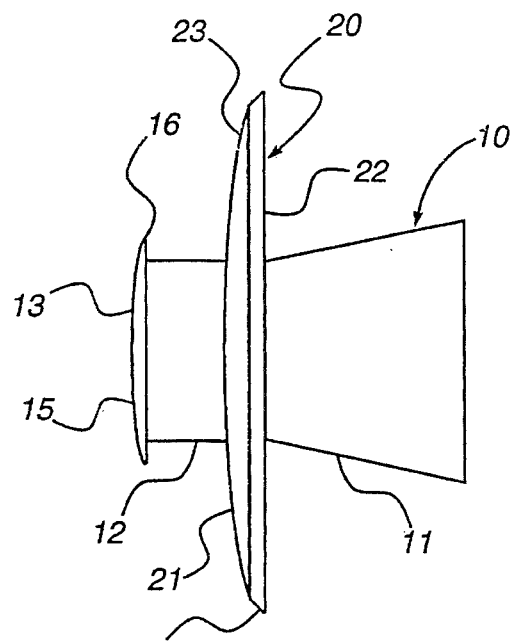
FIG. 2 is a side elevational view of the preferred embodiment of the present invention shown in FIG. 1.

Referring to FIGS. 1 and 2, the corneal prosthesis is illustrated having an optical core member 10 and a skirt member 20. The core member 10 is made of an alloplastic material and preferably intraocular grade polymethylmethacrylate. The optical member 10 is of a substantially frustoconical shape with a posterior substantially conical section 11, and preferably an anterior substantially cylindrical section 12 with a length of 0.8 to 1.2 millimeters. A first anterior end portion 13 is integral with the anterior cylindrical section 12, and a second posterior end portion 14 is integral with the posterior cone section 11. The first anterior end portion 13 has an optical surface 15 acting as a lens, and has an anterior flange 16 extending at least 0.5 millimeter and preferably less than 1.0 millimeter beyond the periphery of the anterior section 12. The posterior conical section 11 has an integral second posterior end portion 14 having an optical surface 17. The core member 10 is typically about 8 millimeters in length, sufficient to avoid the retroprosthesis membrane from growing over the optical surface 17 of the second posterior end portion 14.

A peripheral groove 18 is preferably provided in the optical core member 10 between the posterior cone section 11 and the anterior cylindrical section 12. The groove 18 is capable of holding the skirt member 20 in position peripheral about the optical core member 10 without the use of adhesive material. Groove 18 is preferably 0.25 to 0.50 millimeter deep, and 0.15 to 0.30 millimeter wide depending on the thickness of skirt member 20. Preferably the width of groove 18 is less than 0.05 millimeter larger than the thickness of the skirt member 20.

Skirt member 20 is made of a hydrophilic, porous semi-flexible material capable of vascular invasion and formation of fibrous tissue within the matrix of the material when implanted into an intralamellar pocket in the cornea of an eye. The skirt member 20 is preferably made of a material selected from the group consisting of porous polytetrafluoroethylene, porous polytetrafluoroethylene carbon and porous polytetrafluoroethylene aluminum oxide fibers (trade name Proplast), with polytetrafluoroethylene aluminum oxide fibers being the most preferred. Proplast has been made by Vitek, Inc. in Houston, Tex., and is described in U.S. Pat. Nos. See U.S. Pat. Nos. 3,992,725, 4,118,532, 4,129,470 and 4,209,480.

The skirt member 20 has a total contact area on the anterior and posterior surfaces 21 and 22 of at least about 100 square millimeters, and preferably has an exterior diameter of at least about 9.5 millimeters and most desirably about 10 to 11 millimeters. "Semi-flexible" within the present context means essentially that the skirt member 20 preferably has a flexure modulus (i.e., unit flexibility) corresponding to a polytetrafluoroethylene aluminum oxide fiber sheet between 0.15 and 0.30 millimeter in thickness such that the skirt member has flexibility characteristics suitable to resist extrusion of the prosthesis on the one hand and, on the other hand, resist pressure necrosis of surrounding eye tissue upon implantation of the prosthesis. The contact area of the anterior and posterior surfaces 21 and 22 of the skirt member 20 provides for long term stabilization of the prosthesis upon implantation. The flexure modulus of the skirt member 20 provides for distribution of the force reactive to the extrusion force on the core member 10 over the contact area of the anterior and posterior surfaces 21 and 22 of the skirt member 20, and provides further long-term stabilization and avoids pressure necrosis. The vascularization of the skirt member 20 and the conjunctiva vessels on the surface bring serum antiproteases to prevent enzymatic degradation of the tissue surrounding the optical core member 10.

Figure 3:
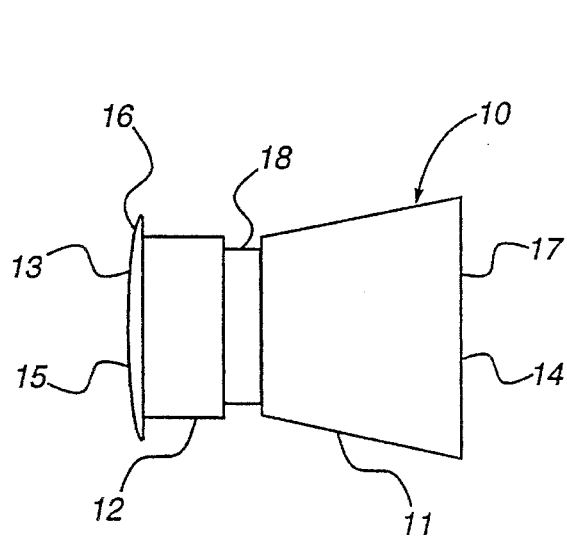
FIG. 3 is a side elevational view of the preferred embodiment of the optical core member of the preferred embodiment of the present invention shown in FIG. 1.
Figure 4:
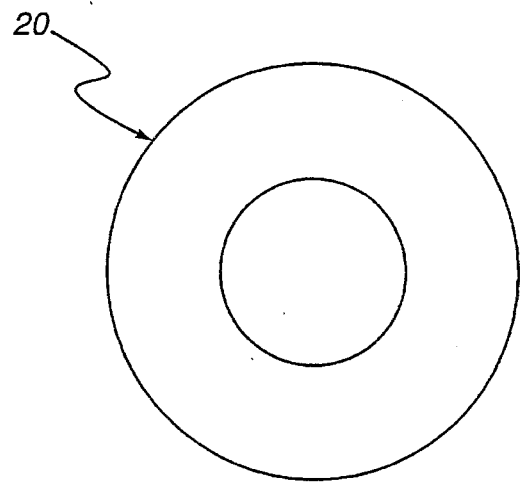
FIG. 4 is an elevational view of the skirt of the preferred embodiment of the present invention shown in FIG. 1.

When implanted, the shape of the posterior conical section 11 forces the posterior lamella of the cornea toward the skirt member 20, holding the posterior lamella against the posterior contact surface 22 of the skirt member 20. This enhances tissue invasion of the skirt member 20, providing further stability for the prosthesis, and seals the cornea posterior to the optical core member 10. The posterior conical section 11 preferably has a flare of 20 to 30 degrees toward the second posterior end portion 17 of the optical core member 10 as shown in FIG. 3.

As indicated above, the anterior section 12 may be slightly conical, sloping either toward or away from the skirt member 20, and at a different flare angle than the posterior section 11. However, it is preferably substantially cylindrical in shape to be effectively axial force neutral in urging the lamella toward or away from the skirt member 20. Although a force urging the lamella toward the anterior contact surface 21 of the skirt member 20 would in itself be beneficial, the conjunctiva would also be urged away from the anterior flange 16 at the same time. Preferably the forces on the lamella adjacent the anterior section 12 are such as to urge the conjunctiva to grow against the anterior flange 16, but not be so great as to cause enzymatic degradation of the tissue adjacent the anterior flange 16. In any event, the anterior section 12 should be between about 0.8 and 1.2 millimeters in length from the anterior flange 16 to the peripheral groove 18 to enable the optical core member 10 to extend above the anterior surface of the conjunctiva at anterior flange 16 and avoid mechanical movement of the prosthesis by the eyelid.

Preferably, the skirt member 20 is sufficiently large in outer diameter that the skirt member 20 extends to within 2 millimeters and preferably 1 millimeter of the limbus. The proximity of the outer peripheral edge portion 23 of the skirt member 20 to the limbus enhances vascular invasion into the edge portion 23 of the skirt member 20, as a further anchor zone for the prosthesis, and increases chemotaxis and speed and degree of incorporation of the prosthesis into an eye. The radial dimension of the anterior flange 16, together with the length and slope of the anterior section 12, are such that the vascularization of the skirt member 20 and the conjunctival vessels on the surface of an eye adjacent flange 16 bring serum antiproteases to prevent enzymatic degradation of the tissue surrounding the core member 10.

In addition, skirt member 20 preferably has a bevel 24 adjacent edge portions 23. This bevel 24 avoids pressure necrosis, which can result if the reactive pressure forces on the anterior contact surface 21 of skirt member 20 are not well distributed. The bevel 24, therefore, provides a further precaution to avoid postoperative complications.

It should also be evident that core member 10 need not be precisely circular along either the posterior section 11 or the anterior section 12. Because of the use of a trephine to surgically install the core member 10, it is helpful that the anterior and posterior sections of the core member 10 be substantially circular. However, since the cornea is oval in shape, the optimum core member 10 shape for postoperative purposes is more preferably oval. Similarly, skirt member 20 need not be circular, but may be oval in shape to increase the contact area of the anterior and posterior surfaces 21 and 22 to provide further vascularization and stabilization of the skirt member 20 and the corneal prosthesis. It is noted that the operative techniques are not inhibited by a non-circular skirt member.

On implanting, the anterior flange 16 peripheral of the first anterior end portion 13, provides a barrier to growth and movement of the conjunctiva across the optical surface 15 of the core member 10. Anterior flange 16 has prevented overgrowth in all of the implants of the corneal prostheses studied to date, yet provides a seal between the eye and the anterior of the prosthesis. On the other hand, the anterior flange 16 should not extend beyond the periphery of the anterior section 12 of the core member 10 so far as to cause enzymatic degradation of the conjunctival tissue adjacent the anterior flange 16.

EXPERIMENTS WITH THE PREFERRED EMBODIMENTS

The preferred embodiments of the corneal prostheses for experimentation were made entirely within the laboratory. The optical core members were cut from cylinders of intraocular grade polymethylmethacrylate furnished by IOLAB company, the same material used for their injection molded intraocular lenses. These optical core members were turned to 11 millimeters in diameter and cut to 8 millimeters in length. The optical core members were mounted in a contact lens lathe and the anterior lens curve was cut in the anterior surface 15 of the first anterior end portion 13. The optical core members were then lathed to the appropriate dimensions including the anterior flange 16, the posterior conical section 11, and the peripheral groove 18 to hold the skirt member 20. The anterior and posterior surfaces 15 and 17 were polished using conventional contact lens techniques. Skirt members 20 of polytetrafluoroethylene aluminum oxide fiber sheets of 10 millimeters in diameter were cut from sheets of 0.2 millimeter thick Proplast. Four point five (4.5) millimeter diameter holes were placed in the center of each skirt member 20 using a trephine, and the outside edge of each skirt member 20 was hand beveled at anterior contact surface 22 as shown in FIG. 2. The skirt members 20 were then forced onto the core member 10 until they snapped into the peripheral groove 18.

Cats were chosen as the experimental animal because of the similarity of the cat cornea to the human cornea, the fastidiousness of the species, the long life span for retention studies, and the ease of handling for daily or biweekly examination. Eleven cats were prepared, using general anesthesia, for prosthesis implant by removal of the nictitating membrane from one eye. To prepare for implant of the prosthesis, the lens of that eye was removed by phacoemulsification and twelve sutures of 9-0 black silk were placed radially in the cornea extending from the limbus into the cornea about 4 millimeters. The sutures were tied and the knots left on the surface of the cornea to promote vascularization of the cornea. This was done in only one eye of each cat to comply with ARVO animal research standards.

Two weeks following the above preparatory procedure, the sutures were removed. Corneas were now vascularized to the central end of the sutures. A 360 degree peritomy was made at the limbus and the entire corneal and limbal epithelium was removed using heptanol and scraping. Total removal was verified using fluorescein staining. A ⅔ thickness corneal groove was made for 5 clock hours at the temporal limbus. Blunt scissors were used to create a lamellar pocket including the entire cornea. At this point a stab incision was made in the contralateral limbus.

The anterior chambers of five of the eleven eyes were then injected with heparin (10,000 USP units per amount) to avoid clotting of the aqueous upon opening an eye. A 4.5 millimeter trephine was used to make a full thickness hole through the center of both layers of the cornea. The skirt member 20 was then placed into the pocket through the limbal opening and the prosthesis centered. It was manipulated until the anterior cylindrical section 12 of the core member 10 was through the anterior lamella hole and the posterior conical section 11 was through the hole in the posterior layer. The anterior chamber was reformed with balanced salt or heparin to force the posterior lamella onto the core member 10 and into contact with the posterior contact surface 22 of the skirt member 20. The conjunctiva was then closed in a double layer fashion to cover the prosthesis and the cornea. Relaxing incisions were made in the peripheral conjunctiva as needed to prevent traction on the wound. Neosporin ointment was used at the end of surgery and daily for three weeks.

Nine of the eleven prostheses were retained by the cats for the duration of the study of 28 weeks. Two prostheses extruded after eight and eleven weeks, respectively, in one cat's eye with and without a heparin injection. Examination of the two eyes where the prostheses extruded showed inflammation and likely infection. Examination of the nine eyes, with the prostheses retained for the duration of the study, showed good incorporation and stabilization of the prostheses in the eyes, and there were no indications of inflammation or infection. This study demonstrated the stability of the improved corneal prosthesis of the present invention in a difficult model, and demonstrates the retention qualities and utility of the prosthesis for human eyes.

While presently preferred embodiments to practice the invention are shown and described with particularity in connection with the accompanying drawings, the invention may otherwise be embodied within the scope and spirit of the following claims:

What is claimed is

1. A corneal prosthesis comprising:
   (a) an optical core member capable of optically transmitting light from an exterior of an eye to a retina of the eye, said optical core member being formed from an alloplastic material, said optical core member comprising a posterior section, first optical end portion, and an anterior section adjacent to said first optical end portion, said first optical end portion having an anterior flange portion extending peripherally at least about 0.5 millimeter beyond the periphery of said anterior section and said posterior section having a substantially frustoconical shape; and
   (b) a skirt member extending peripherally about and attached to the optical core member in spaced relation to the first optical end portion and capable of being implanted into a lamellar pocket in an eye, said skirt member being formed from a hydrophilic porous material capable of receiving vascular invasion and formation of fibrous tissue therein and having anterior and posterior contact surfaces,
   whereby, upon implantation of the corneal prosthesis in an eye, the substantially frustoconical shape of the optical core member engages and urges lamellar eye tissue toward the posterior contact surface of the skirt member.

2. A corneal prosthesis as set forth in claim 1 wherein the optical core member is made of intraocular grade polymethylmethacrylate.

3. A corneal prosthesis as set forth in claim 1 wherein the material from which the skirt member is formed is selected from the group consisting of porous polytetrafluoroethylene, porous polytetrafluoroethylene carbon and porous polytetrafluoroethylene aluminum oxide fibers.

4. A corneal prosthesis as set forth in claim 1 wherein the optical core member has a peripheral groove capable of mechanically attaching the skirt member to the optical core member.

5. A corneal prosthesis as set forth in claim 4 wherein the anterior section is between about 0.8 and 1.2 millimeters in length from the anterior flange to the peripheral groove.

6. A corneal prosthesis as set forth in claim 1 wherein the skirt member is at least about 9.5 millimeters in outer diameter.

7. A corneal prosthesis as set forth in claim 1 wherein the skirt member is formed from material having a flexure modulus corresponding to porous polytetrafluoroethylene aluminum oxide fiber sheet between about 0.15 and 0.30 millimeter in thickness such that the skirt member has flexibility characteristics suitable to resist extrusion of the corneal prosthesis and pressure necrosis of surrounding eye tissue when the corneal prosthesis is implanted in an eye.

8. A corneal prosthesis as set forth in claim 1 wherein the skirt member is a porous polytetrafluoroethylene aluminum oxide fibrous sheet having a thickness between about 0.15 and 0.30 millimeter.

9. A corneal prosthesis as set forth in claim 1 wherein the skirt member has a peripheral bevel portion around the anterior contact surface.

10. A corneal prosthesis as set forth in claim 1 wherein the anterior and posterior contact surfaces of the skirt member have a total contact area greater than about 100 square millimeters.

11. A corneal prosthesis comprising:

(a) an optical core member capable of optically transmitting light from an exterior of an eye to a retina of the eye, said optical core member being formed from an alloplastic material, said optical core member comprising a first optical end portion and a second optical end portion capable of being positioned toward the retina of the eye;

(b) said optical core member further comprising an anterior substantially cylindrical section adjacent to the first optical end portion and a posterior substantially frustoconical section adjacent said anterior section and flared toward the second optical end portion, said first optical end portion having an anterior flange portion extending peripherally at least about 0.5 millimeter beyond the periphery of said anterior section; and (c) a skirt member extending peripherally about and attached to the optical core member in spaced relation to the first optical end portion and capable of being implanted into a lamellar pocket in an eye, said skirt member being formed from a hydrophilic porous material capable of receiving vascular invasion and formation of fibrous tissue therein and having anterior and posterior contact surfaces, whereby, upon implantation of the corneal prosthesis in an eye, the posterior substantially frustoconical section of the optical core member engages and urges lamellar eye tissue toward the posterior contact surface of the skirt member.

12. A corneal prosthesis as set forth in claim 11 wherein the optical core member is made of intraocular grade polymethylmethacrylate.

13. A corneal prosthesis as set forth in claim 11 the material from which wherein the skirt member is formed is selected from the group consisting of porous polytetrafluoroethylene, porous polytetrafluoroethylene carbon and porous polytetrafluoroethylene aluminum oxide fibers.

14. A corneal prosthesis as set forth in claim 11 wherein the optical core member has a peripheral groove capable of mechanically attaching the skirt member to the optical core member positioned between the anterior cylindrical section and the posterior frustoconical section.

15. A corneal prosthesis as set forth in claim 14 wherein the anterior section is between about 0.8 and 1.2 millimeters in length from the anterior flange to the peripheral groove.

16. A corneal prosthesis as set forth in claim 11 wherein the skirt member is at least about 9.5 millimeters in outer diameter.

17. A corneal prosthesis as set forth in claim 11 wherein the skirt member is formed from material having a flexure modulus corresponding to a porous polytetrafluoroethylene aluminum oxide fiber sheet between about 0.15 and 0.30 millimeter in thickness such that the skirt member has flexibility characteristics suitable to resist extrusion of the corneal prosthesis and pressure necrosis of surrounding eye tissue when the corneal prosthesis is implanted in an eye.

18. A corneal prosthesis as set forth in claim 11 wherein the skirt member is a porous polytetrafluoroethylene carbon fibrous sheet having a thickness between about 0.15 and 0.30 millimeter.

19. A corneal prosthesis as set forth in claim 11 wherein the skirt member has a peripheral bevel portion around the anterior contact surface.

20. A corneal prosthesis as set forth in claim 11 wherein the anterior and posterior contact surfaces of the skirt member have a total contact area greater than about 100 square millimeters.

* * * * *